(12) United States Patent
Tippey et al.

(10) Patent No.: US 7,504,550 B2
(45) Date of Patent: Mar. 17, 2009

(54) CONDUCTIVE POROUS MATERIALS

(75) Inventors: Darold Dean Tippey, Neenah, WI (US); Thomas Michael Ales, III, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 414 days.

(21) Appl. No.: 11/514,434

(22) Filed: Aug. 31, 2006

(65) Prior Publication Data
US 2008/0058744 A1    Mar. 6, 2008

(51) Int. Cl.
*A61F 13/15* (2006.01)
(52) U.S. Cl. .................... 604/358; 442/400
(58) Field of Classification Search ............ 442/400; 604/358
See application file for complete search history.

(56) References Cited

U.S. PATENT DOCUMENTS

| | | | |
|---|---|---|---|
| 3,849,241 A | 11/1974 | Butin et al. |
| 4,100,324 A | 7/1978 | Anderson et al. |
| 4,587,154 A | 5/1986 | Hotchkiss et al. |
| 4,604,313 A | 8/1986 | McFarland et al. |
| 4,655,757 A | 4/1987 | McFarland et al. |
| 4,724,114 A | 2/1988 | McFarland et al. |
| 4,754,264 A | 6/1988 | Okada et al. |
| 5,047,283 A | 9/1991 | Leatherman et al. |
| 5,112,900 A | 5/1992 | Buddenhagen et al. |
| 5,114,781 A | 5/1992 | Morman |
| 5,116,662 A | 5/1992 | Morman |
| 5,131,141 A | 7/1992 | Kawaguchi |
| 5,350,624 A | 9/1994 | Georger et al. |
| 5,407,715 A | 4/1995 | Buddenhagen et al. |

(Continued)

FOREIGN PATENT DOCUMENTS

EP          1 047 033 A1     10/2000

(Continued)

OTHER PUBLICATIONS

"Conductive and Resistive Inks/Circuit Technology," Methode Electronics Inc., Internet web page "http://www.methodedevelopment.com/inking/", 2006, available prior to the filing date of the current application, 1 page.

(Continued)

*Primary Examiner*—Lynda Salvatore
(74) *Attorney, Agent, or Firm*—Paul Y. Yee; Bryan R. Rosiejka; Vincent T. Kung (57) ABSTRACT

A limited use, disposable article (20), comprises a matrix-substrate (22), and an electrically-conductive region (24) of a separately provided, electrically-conductive material that has been operatively applied to the matrix-substrate from a viscous configuration of the electrically-conductive material. The matrix-substrate includes a first matrix-region (26), and at least a second matrix-region (28). At least the second matrix-region (28) can include a treatment that provides for an operative formation of a selected resistivity in the electrically-conductive region. The first matrix-region (26) has a high resistivity, and the electrically-conductive region (24) is positioned operatively adjacent the second matrix-region (28). The electrically-conductive region (24) has a low resistivity, as determined when the electrically-conductive region is positioned operatively adjacent the second matrix-region and configured for its intended use.

20 Claims, 4 Drawing Sheets

U.S. PATENT DOCUMENTS

| | | | |
|---|---|---|---|
| 5,486,166 | A | 1/1996 | Bishop et al. |
| 5,490,846 | A | 2/1996 | Ellis et al. |
| 5,492,598 | A | 2/1996 | Hermans et al. |
| 5,591,298 | A | 1/1997 | Goodman et al. |
| 5,646,369 | A | 7/1997 | Miska et al. |
| 5,743,999 | A | 4/1998 | Kamps et al. |
| 5,763,058 | A | 6/1998 | Isen et al. |
| 5,808,554 | A | 9/1998 | Shuminov |
| 5,820,973 | A | 10/1998 | Dodge, II et al. |
| 5,883,028 | A | 3/1999 | Morman et al. |
| 5,900,452 | A | 5/1999 | Plamthottam |
| 6,010,771 | A | 1/2000 | Isen et al. |
| 6,021,050 | A | 2/2000 | Ehman et al. |
| 6,200,250 | B1 | 3/2001 | Janszen |
| 6,288,159 | B1 | 9/2001 | Plamthottam |
| 6,306,514 | B1 | 10/2001 | Weikel et al. |
| 6,311,350 | B1 | 11/2001 | Kaiserman et al. |
| 6,362,389 | B1 | 3/2002 | McDowall et al. |
| 6,517,671 | B2 | 2/2003 | Couillard et al. |
| 6,552,245 | B1 | 4/2003 | Roessler et al. |
| 6,641,134 | B1 | 11/2003 | Dobbertin et al. |
| 6,824,857 | B2 | 11/2004 | Lochun et al. |
| 2002/0145525 | A1 | 10/2002 | Friedman et al. |
| 2004/0207530 | A1 | 10/2004 | Nielsen |
| 2006/0004336 | A1 | 1/2006 | Zhang et al. |
| 2007/0142797 | A1 | 6/2007 | Long et al. |
| 2008/0054408 | A1 | 3/2008 | Tippey et al. |
| 2008/0057693 | A1 | 3/2008 | Tippey et al. |

FOREIGN PATENT DOCUMENTS

| | | |
|---|---|---|
| EP | 1 622 435 A1 | 2/2006 |
| FR | 2 582 812 A1 | 12/1986 |
| GB | 2 151 272 A1 | 7/1985 |
| JP | 55-115397 A | 9/1980 |
| JP | 58-020158 A | 2/1983 |
| JP | 60-208888 A | 10/1985 |
| JP | 60-208894 A | 10/1985 |
| JP | 2005-116624 A | 4/2005 |
| WO | WO 03/002346 A2 | 1/2003 |

OTHER PUBLICATIONS

"Manufacturing Process for Printed Circuit Boards," Advanced Circuits, Internet web page"http://www.4pcb.com/american_made_cheap_printed_boards_manufacturing_process.htm", available prior to the filing date of the current application, pp. 1-2.

"Ultem® Resin for Flexible Printed Circuit Applications," *IP.com Journal*, vol. 3, No. 2, 2003, available at Internet web page "http://www.priorartdatabase.com/IPCOM/000010843/" pp. 1-6.

Calvert, Paul, "Inkjet Printing for Materials and Devices," *Chem. Mater.*, vol. 13, No. 10, 2001, pp. 3299-3305.

Mills, Ross N., "Linear Positioners Drive Ink Jets," *Control Engineering*, Feb. 1, 2006, available at Internet web page "http://www.controleng.com/article/CA6303931.html", pp. 1-3.

American Society for Testing Materials (ASTM) Designation: D1388-96, "Standard Test Method for Stiffness of Fabrics," pp. 313-318, published Jun. 1996.

American Society for Testing Materials (ASTM) Designation: D1525-06, "Standard Test Method for Vicat Softening Temperature of Plastics," pp. 1-9, published Apr. 2006.

American Society for Testing Materials (ASTM) Designation: D3039/D3039M-95a, "Standard Test Method for Tensile Properties of Polymer Matrix Composite Materials," pp. 99-109, published Oct. 1995.

American Society for Testing Materials (ASTM) Designation: D3518/D3518M-94, "Standard Test Method for In-Plane Shear Response of Polymer Matrix Composite Materials by Tensile Test of a ±45° Laminate," pp. 1-7, published Jan. 1995.

American Society for Testing Materials (ASTM) Designation: F1896-98 (Reapproved 2004), "Test Method for Determining the Electrical Resistivity of a Printed Conductive Material," pp. 1-3, published Jun. 2004.

Federal Test Method Standard (FTMS) No. 191A, Method 5514, "Water Resistance of Cloth; Low Range, Hydrostatic Pressure Method," Jul. 20, 1978, 3 pages.

"Spunlaced Fabric," *Dictionary of Fiber & Textile Technology*, Hoechst Celanese Corporation, 1989, p. 149.

Lawrence, K.D. et al., "An Improved Device For the Formation of Superfine, Thermoplastic Fibers," *NRL Report 5265*, U.S. Naval Research Laboratory, Washington, D.C., Feb. 11, 1959, pp. 1-7.

Pourdeyhimi, Behnam et al., "Printing Electric Circuits onto Nonwoven Conformal Fabrics," *National Textile Center Research Briefs—Fabrication Competency*, Jun. 2005, 2 pages.

Sims, Graham D., "Three- and Four-Point Flexure," Chapter 18, Section 7.3, *Handbook of Polymer Testing*, edited by Roger Brown, Marcel Dekker Inc., New York, 1999, p. 416.

Wente, V.A. et al., "Manufacture of Superfine Organic Fibers," *NRL Report 4364*, U.S. Naval Research Laboratory, Washington, D.C., May 25, 1954, pp. 1-15.

CONDUCTIVE POROUS MATERIALS

FIELD OF THE INVENTION

The present invention relates to electrical circuits formed on a flexible substrate. More particularly, the present invention pertains to electrical circuits formed on a substrate having a high degree of surface porosity.

BACKGROUND OF THE INVENTION

Electrical circuits have been printed or otherwise applied to flexible substrates, such as paper, woven fabrics, nonwoven fabrics and polymer films. The electrical circuits have incorporated conductive inks applied with various ink-printing techniques, and various products, such as covers, badges, labels and tags, have incorporated the printed circuits. In particular arrangements, the printed circuits have been employed in hygienic products, such as drapes, gowns, garments, personal care absorbent products, and the like. In other arrangements, electrical/electronic circuitry has been employed to provide sensors located in selected personal care products, such as wetness sensors in disposable infant diapers.

Conventional printed circuit configurations formed on substrates having high levels of surface porosity, however, have continued to exhibit problems. When the conductive inks have been printed on porous materials, the level of electrical conductivity has been excessively degraded. As a result, there has been a continuing need for improved configurations of conductive circuits printed onto porous materials.

BRIEF DESCRIPTION OF THE INVENTION

Generally stated, the present invention provides a distinctive limited use, disposable article, comprising a matrix-substrate; and an electrically-conductive region of a separately provided, electrically-conductive material that has been operatively applied to the matrix-substrate from a viscous configuration of the electrically-conductive material. The matrix-substrate includes a first matrix-region, and at least a second matrix-region. At least the second matrix-region can include a treatment that provides for a formation of a selected resistivity in the electrically-conductive region. The first matrix-region has a high resistivity, and the electrically-conductive region is positioned operatively adjacent the second matrix-region. The electrically-conductive region has a low resistivity, as determined when the electrically-conductive region is positioned operatively adjacent the second matrix-region and configured for its intended use. In particular aspects, the matrix-substrate can include a substantially continuously extending network of matrix-material; and the high resistivity of the first matrix region can be at least about an order of magnitude greater than the resistivity of the electrically-conductive region.

By incorporating its various aspects and features, the method can provide a more effective printing of electrical conductors on porous or semi-porous, materials with a reduced loss of conductivity. The method can help form a flexible continuous base region to support electrical connections with more uniform electrical continuity. Additionally, the method can be more readily employed with ordinary ink formulations, and with ordinary printing equipment.

BRIEF DESCRIPTION OF THE DRAWINGS

The invention will be better understood by reference to the following description of the invention taken in conjunction with the accompanying drawings, wherein.

DETAILED DESCRIPTION OF THE INVENTION

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

By the terms "particle," "particles," "particulate," "particulates" and the like, it is meant that the material is generally in the form of discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for inclusion herein. The terms "particle" or "particulate" may also include an agglomeration comprising more than one individual particle, particulate or the like.

Additionally, a particle, particulate or any desired agglomeration thereof may be composed of more than one type of material.

As used herein, the term "nonwoven" refers to a fabric web that has a structure of individual fibers or filaments which are interlaid, but not in an identifiable repeating manner.

As used herein, the terms "spunbond" or "spunbonded fiber" refer to fibers which are formed by extruding filaments of molten thermoplastic material from a plurality of fine, usually circular, capillaries of a spinneret, and then rapidly reducing the diameter of the extruded filaments.

As used herein, the phrase "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers.

"Coform" as used herein is intended to describe a blend of meltblown fibers and cellulose fibers that is formed by air forming a meltblown polymer material while simultaneously blowing air-suspended cellulose fibers into the stream of meltblown fibers. The meltblown fibers containing wood fibers are collected on a forming surface, such as provided by a foraminous belt. The forming surface may include a gas-pervious material, such as spunbonded fabric material, that has been placed onto the forming surface.

As used herein, the phrase "absorbent article" refers to devices which absorb and contain body liquids, and more specifically, refers to devices which are placed against or near the skin to absorb and contain the various liquids discharged from the body. The term "disposable" is used herein to describe absorbent articles that are not intended to be laundered or otherwise restored or reused as an absorbent article after a single use. Examples of such disposable absorbent articles include, but are not limited to: health care related products including surgical drapes, gowns, and sterile wraps; personal care absorbent products such as feminine hygiene products (e.g., sanitary napkins, pantiliners, tampons, interlabial devices and the like), infant diapers, children's training pants, adult incontinence products and the like; as well as absorbent wipes and covering mats.

Disposable absorbent articles such as, for example, many of the personal care absorbent products, can include a liquid pervious topsheet, a substantially liquid impervious backsheet joined to the topsheet, and an absorbent core positioned and held between the topsheet and the backsheet. The topsheet is operatively permeable to the liquids that are intended to be held or stored by the absorbent article, and the backsheet may be substantially impermeable or otherwise operatively impermeable to the intended liquids. The absorbent article may also include other components, such as liquid wicking layers, liquid distribution layers, barrier layers, and the like, as well as combinations thereof. Disposable absorbent articles and the components thereof, can operate to provide a body-facing surface and a garment-facing surface. As used herein, "body-facing surface" means that the surface of the article or component which is intended to be disposed toward or placed adjacent to the body of the wearer during ordinary use, while the "outward surface" or "outward-facing surface" is on the opposite side, and is intended to be disposed to face away from the wearer's body during ordinary use. The outward surface may be arranged to face toward or placed adjacent to the wearer's undergarments when the absorbent article is worn.

With reference to FIGS. 1 through 4, a distinctive limited use, disposable article 20, can include a matrix-substrate 22; and an electrically-conductive region 24 of a separately provided, electrically-conductive material that has been operatively applied to the matrix-substrate 22 from a viscous configuration of the electrically-conductive material. For example, the electrically-conductive material can be deposited directly or indirectly onto the matrix-substrate. The matrix-substrate includes a first matrix-region 26, and at least a second matrix-region 28. The second matrix-region may optionally have a structure that differs from the first matrix-region. In a particular aspect, at least the second matrix-region 26 can include a treatment that provides for an operative formation of a selected resistivity in the electrically-conductive region. The first matrix-region has a high resistivity value. The electrically-conductive region 24 is positioned operatively adjacent the second matrix-region 28; and the electrically-conductive region 24 has an operative, significantly low resistivity value, as compared to the resistivity value of the first matrix-region 26. The resistivity value of the electrically-conductive region 24 is determined when the electrically-conductive region has been positioned operatively adjacent the second matrix-region 28 and has been configured for its intended use.

In particular aspects, the matrix-substrate 22 can include a substantially continuously extending network of matrix-material; and the high resistivity of the first matrix region 26 can be at least about an order of magnitude greater than the resistivity of the electrically-conductive region 24.

By incorporating its various aspects and features, alone or in desired combinations, the method of the invention can efficiently and economically provide a more effective printing of electrically-conductive circuit paths on porous or semi-porous materials with a reduced loss of conductivity. For example, the method can more effectively integrate electrical conductors and circuits into health and hygiene garments constructed wholly or partially of porous fabric or foam materials. The method can help form a flexible continuous base region to support electrical connections with more uniform electrical continuity. Additionally, the method can be more readily employed with ordinary ink formulations, and with ordinary printing equipment.

The limited use, disposable article 20 can have various configurations. Examples of such articles can, for example, include disposable hygienic articles, such as drapes, sheets, caps, gowns, garments, personal hygiene products, adult incontinence products, feminine hygiene products, infant diapers, children's training pants and the like.

Particular article configurations can, for example, help provide a new generation of SMART disposable articles that are capable of providing real-time sensing and diagnostic functions. The articles can, for example, be configured to provide a wetness indicator for a product having a semi-durable alarm component placed on the product with internal electrodes printed directly on the product bodyside liner. In other arrangements, the article may be configured to produce an EKG jacket, which has an internal wiring harness incorporated into the disposable material used to construct the jacket. The jacket can also have a conductive pathway through the thickness of the jacket material which operatively interconnects the wiring harness to an electrical interface located on an outside surface of the jacket. The interface can, in turn, operatively connect to an EKG monitoring device or system. In still other arrangements, the article may be configured to include electrical conductors connected to sensors embedded in disposable articles, such as disposable hospital gowns, to monitor selected bodily functions.

The article 20 can include at least one flexible substrate, such as a flexible matrix-substrate 22. The substrate can have sufficient flexibility to allow a convenient use in an ordinary, disposable article. Desirably, the substrate can have a flexibility that is no stiffer than the flexibility of a typical layer of felted or woven fabric that may be employed in ordinary, heavy winter clothing.

In another aspect, the substrate can have a significantly high degree of surface porosity. In particular arrangements, the highly porous surface of the substrate can have a percentage of open area which is 50% or more. For example, the porous substrate may include a cellular foam material, an open-cell foam material, an airlaid fibrous web, a nonwoven fabric or the like. Suitable nonwoven fibrous webs or fabrics may include airlaid fibrous webs that have been stabilized with binder materials, coform materials, spunbond fabrics, bonded carded web fabrics, through-air bonded carded webs, or the like.

A suitable technique for measuring and determining the level of surface porosity can include conventional image-analysis systems. In a desired technique, the surface of a matrix-substrate can be imaged with a scanning electron microscope (SEM) equipped with a backscatter detector to acquire high contrast images where the pores appear as black regions, and the materials of the matrix-substrate (e.g. fibers) appear as white regions. Image analysis can subsequently be performed on the images to measure the sizes and overall level of surface porosity. The SEM method has been referred to as Backscatter Electron Detection/High Contrast (BSE/HICON) imaging. A series of digital surface images are acquired (e.g. 12 images) at a suitable magnification, which will be dependent on the size of the pores and matrix-substrate material. Typical magnifications can be within the range of about 25-500×, and pixel resolutions are normally near 1024×1024, or greater. Details regarding the process of BSE/HICON imaging have been described in U.S. Pat. No. 5,743,999 to Kamps, et al.; and U.S. Pat. No. 5,492,598 to Hermans, et al., each of which is incorporated by reference in their entirety in a manner that is consistent herewith. Although these particular documents describe analyses of cross-sections through a material, similar procedures and similar equipment (e.g. without liquid nitrogen cross-sectioning, edge-view mounting, and photo-editing) may be employed to assess the porosity of a major facing-surface of a selected material. It should also be appreciated that the acquisition of digital images may be substituted for the use of Polaroid film.

Once digital BSE/HICON images are acquired, they can be electronically transferred directly to an image analysis system for subsequent measurements. Leica Micro-Systems QWIN version 3.2 image analysis software can be implemented along with an appropriate, readily written QUANTIMET User Interactive Programming System (QUIPS) routine to perform conventional pore size measurements, and determine the open area provided by the porous regions. Typically, the pore sizes can be measured in units of area or calculated into a derived parameter; such as equivalent-circular diameter (i.e., square root of the quantity, 4*Area/π), or equivalent-hydraulic diameter (i.e., 4*Area/Perimeter). Other more sophisticated methods of determining surface pore size can also be used (e.g., convoluted pore width). The overall level of surface porosity can be determined for each BSE/HICON image by measuring the percentage of pores within the entire image.

To provide desired performance, the matrix-substrate 22 can have selected levels of basis weight. In particular aspects, the basis weight of the matrix-substrate can be at least a minimum of about 5 $g/m^2$. The basis weight can alternatively be at least about 10 $g/m^2$, and can optionally be at least about 15 $g/m^2$ to provide desired benefits. In other aspects, the basis weight can be up to a maximum of about 130 $g/m^2$, or more. The basis weight can alternatively be up to about 45 $g/m^2$ or 60 $g/m^2$, and can optionally be up to about 30 $g/m^2$ to provide desired effectiveness. Accordingly, the above-described levels of basis weight can also be provided to the first matrix-region 26

In desired configurations, the matrix-substrate can include a substantially continuously extending network of matrix-material. Additionally, the matrix-material can be configured to provide an interconnected plurality of matrix elements. The matrix elements can, for example, include fibers, cellular-wall elements, network elements of spun, blown or extruded materials, polymer network elements or the like, as well as combinations thereof.

In a particular configuration, the matrix-material can be configured to provide interconnected plurality of fibers, and the fibers can be configured to provide an operative woven or nonwoven fabric. Suitable nonwoven fabrics can, for example, include spunbond fabrics, meltblown fabrics, coform materials, hydroentangled fabrics, stretch-bonded-laminate fabrics, elastomeric fabrics, elastomeric fabric laminates or the like, as well as combinations thereof.

In another aspect, the interconnected plurality of fibers in the fibrous matrix-material can be configured to provide a first fibrous matrix-region 26, and a second fibrous matrix-region 28. As representatively shown, the first fibrous matrix-region 26 can include a first fibrous layer or other fibrous region; and the second matrix-region 28 can include a second fibrous layer or other fibrous region.

The electrically-conductive region 24 of the separately provided, electrically-conductive material can be deposited onto the matrix substrate 22, and in particular arrangements, the electrically-conductive material can be deposited onto the appointed, second matrix-region 28 of the matrix substrate. The separately provided, electrically-conductive material can be applied by employing any operative technique, and the desired viscous configuration of the electrically-conductive material can typically be an operative, generally liquid-form of the electrically-conductive material. In a desired arrangement, the liquid configuration of the electrically-conductive material can include an electrically-conductive ink material. The liquid or other viscous configuration of the electrically-conductive material can be applied by employing any operative printing technique or system.

An individual, electrically-conductive material may include an electrically-conductive ink. The conductive ink includes electrically-conductive materials, and can be formulated for printing onto the selected substrate using various printing processes. The conductive ink typically includes a vehicle including one or more resins and/or solvents. Various other ink additives known in the art, e.g., antioxidants, leveling agents, flow agents and drying agents, may be included in the conductive ink. The conductive ink can be in the form of a paste, slurry or dispersion. The ink generally also includes one or more solvents that readily can be adjusted by the skilled practitioner for a desired rheology. The ink formulation is desirably mixed in a grinding mill to sufficiently wet the conductive particles with the vehicle, e.g., solvent and resin.

The conductive material can include silver, copper, gold, palladium, platinum, carbon, or combinations of these particles. The average particle size of the conductive material can be within the range of between about 0.5 µm and about 20 µm. Desirably, the average particle size can be between about 2

μm and about 5 μm. Alternatively, the average particle size can be about 3 μm. The amount of conductive material in the conductive trace or circuit-path can be between about 60% and about 90%, on a dry weight basis. Desirably, the amount of conductive material in the conductive trace can be between about 75% and about 85%, on a dry weight basis.

The electrically-conductive particles can be flakes and/or powders. In particular arrangements, the conductive flakes have a mean aspect ratio of between about 2 and about 50, and desirably between about 5 and about 15. The aspect ratio is a ratio of the largest linear dimension of a particle to the smallest linear dimension of the particle. For example, the aspect ratio of an ellipsoidal particle is the diameter along its major axis divided by the diameter along its minor axis. For a flake, the aspect ratio is the longest dimension across the length of the flake divided by its thickness.

Suitable conductive flakes may include those sold by METALOR (a business having offices located in Attleboro, Mass., U.S.A.) under the following trade designations: P185-2 flakes having a particle size distribution substantially between about 2 μm and about 18 μm; P264-1 and P264-2 flakes having particle size distributions substantially between about 0.5 μm and about 5 μm; P204-2 flakes having a particle size distribution substantially between about 1 μm and about 10 μm; P204-3 flakes having a particle size distribution substantially between about 1 μm and about 8 μm; P204-4 flakes having a particle size distribution substantially between about 2 μm and about 9 μm; EA-2388 flakes having a particle size distribution substantially between about 1 μm and about 9 μm; SA-0201 flakes having a particle size distribution substantially between about 0.5 μm and about 22 μm and having a mean value of about 2.8 μm; RA-0001 flakes having a particle size distribution substantially between about 1 μm and about 6 μm; RA-0015 flakes having a particle size distribution substantially between about 2 μm and about 17 μm; and RA-0076 flakes having a particle size distribution substantially between about 2 μm and about 62 μm, and having a mean value of about 12 μm.

Suitable silver powders may include those sold by METALOR under the following trade designations: C-0083P powder having a particle size distribution substantially between about 0.4 μm and about 4 μm, and having a mean value of about 1.2 μm; K-0082P powder having a particle size distribution substantially between about 0.4 μm and about 6.5 μm, and having a mean value of about 1.7 μm; and K-1321P powder having a particle size distribution substantially between about 1 μm and about 4 μm.

The conductive ink may include a resin. Suitable resins can, for example, include polymers, polymer blends, fatty acids or the like, as well as combinations thereof. In particular arrangements, alkyd resins may be employed. Examples of such resins include LV-2190, LV-2183 and XV-1578 alkyd resins from Lawter International (a business having offices located in Kenosha, Wis., U.S.A.). Also suitable are Crystal Gloss Metallic Amber resin, Z-kyd resin, and alkali refined linseed oil resin available from Kerley Ink (a business having offices located in Broadview, Ill., U.S.A.). Soy resins, such as those available from Ron Ink Company (a business having offices located in Rochester, N.Y., U.S.A.) are also suitable.

Solvents for use in the conductive ink formulation are well known in the art, and a person can readily identify a number of suitable solvents for use in a particular printing application. Solvents can generally comprise between about 3% and about 40% of the ink by weight on a wet basis. The amount may vary depending on various factors including the viscosity of the resin, the solvation characteristics of the solvent, and the conductive particle size, distribution and surface morphology for any given printing method. Generally, the solvent can be added to the ink mixture until a desired ink rheology is achieved. The desired rheologies can depend on the printing method used, and are well known by skilled printers and ink manufacturers.

The solvent in the conductive ink can include non-polar solvents such as a hydrocarbon solvent, water, an alcohol such as isopropyl alcohol, and combinations thereof. Particular arrangements may employ an aliphatic hydrocarbon solvent. Examples of suitable solvents include ISOPAR H aliphatic hydrocarbon solvent from Exxon Corporation (a business having offices located in Houston, Tex., U.S.A.); EXX-PRINT M71a and EXX-PRINT 274a aliphatic and aromatic hydrocarbon solvent from Exxon Corporation; and MCGEE SOL 52, MCGEE SOL 47 and MCGEE SOL 470 aliphatic and aromatic hydrocarbon solvent from Lawter International (Kenosha, Wis., U.S.A.).

Various printing techniques can be employed to produce an individual, electrically conductive circuit-path or trace. The printing techniques are conventional and commercially available. For example, the electrically-conductive ink can be applied to the selected substrate using printing techniques known in the art for printing inks on paper and other substrates, including, but not limited to, offset-lithographic (wet, waterless and dry), flexographic, rotogravure (direct or offset), intaglio, ink jet, electrophotographic (e.g. laser jet and photocopy), and letterpress printing. These printing methods are desirable because conventional methods for forming traces on circuit boards include multiple steps (e.g., photoresist, cure and etching) are time intensive, environmentally unfriendly, and relatively expensive. Commercial printing presses preferably are used for printing on the substrates of the present invention. Commercial printing presses may require additional drying capability to dry the ink after printing or require modifications to handle polymer films (e.g., to handle electrostatic charge). These types of modifications are known in the art and typically can be ordered when purchasing a commercial printing press. Depending on the printing technology, printing speed in the range of from about 150 feet per minute to about 300 feet per minute readily can be achieved. It is envisioned that even greater printing speeds can be achieved, e.g., about 1000 feet per minute or more.

The electrically-conductive ink can desirably be deposited in a quantity such that the dried conductive trace or circuit-path has a thickness dimension which is within the range of about 1 μm to about 8 μm, depending on the printing process used. For example, a single printing operation which provides an ink film thickness of about 2 μm to about 3 μm is typically sufficient to achieve sufficient conductivity. The conductive ink optionally can be printed on the selected substrate two or more times to deliver more conductive ink to the selected substrate. In particular arrangements, the conductive ink is printed only once to avoid the registration problems that may arise when printing multiple times.

Optionally, the conductive ink may be dried at a selected drying temperature to help form the desired conductive trace or circuit-path. In a particular aspect, the drying can be conducted prior to a step of embedding the trace into its associated, cooperating substrate. The drying temperature is desirably selected to avoid excessive damage to the substrate or barrier layer material.

The conductive ink may be dried at the selected drying temperature to drive off some or all of the solvent or carrier to minimize any bubbles containing trapped solvent, and/or to minimize pin holes or craters from rapid solvent evaporation. The conductive ink can be dried using an oven, such as a convection oven, or using infrared, and radio frequency drying, or ultraviolet (UV) radiation. In a particular arrangement, the heating device may be designed to allow the printed substrate to pass therethrough so that the conductive ink can be dried in a continuous manner to facilitate large-scale production. The drying temperature employed depends on the ink used, the softening temperature of the selected substrate, and the drying time or belt speed. Typical drying temperatures can be within the range of about 125° F. to about 150° F. (about 52° C.-66° C.). When UV is employed, the drying temperature may be at room temperature. After the drying step, the circuit element can be allowed to cool prior to the optional embedding step. Alternatively, the drying step can be achieved continuously with the embedding step as the trace is heated to the drying temperature.

In a desired aspect, at least the second matrix-region 26 can include a treatment that provides for an operative formation of a selected resistivity in the electrically-conductive region, and the selected treatment can be provided by any operative configuration or technique. When providing the second matrix-region 26 of the matrix-substrate 22, the initially-provided material in the second matrix-region may or may not be further modified or adjusted to significantly differ from the first matrix-region 24 of the matrix-substrate.

With reference to FIGS. 1-4, for example, the matrix-substrate 22 can include a first matrix-region 26 and at least a second matrix-region 28, and at least the second matrix-region 28 can be treated to include at least a second, supplemental material 32. In a particular arrangement, the matrix-substrate 22 can include a selected base material 30, and the base material is located in at least the first matrix-region 26. Additionally, the base material 30 may also extend into or may otherwise be located in the second matrix-region 28. At least the second matrix-region 28 includes the supplemental material 32. Optionally, the supplemental material may be configured to extend into the first matrix-region 26. In a desired configuration, the electrically-conductive material can be deposited on or otherwise applied to a selected area of the supplemental material 32 to provide the desired electrically-conductive region 24.

The matrix, base material 30 can, for example, be fibrous and include a first fibrous material. Alternatively, the base material may be non-fibrous. For example, the base material may be a foam material or other cellular material. Typically, the base material includes surface pores, openings, void spaces or other surface-interstices. Accordingly, the first matrix-region 26 can include a first fibrous layer having a plurality of the surface-interstices. The second supplemental material can also be fibrous or substantially non-fibrous, as desired.

Figure 1:
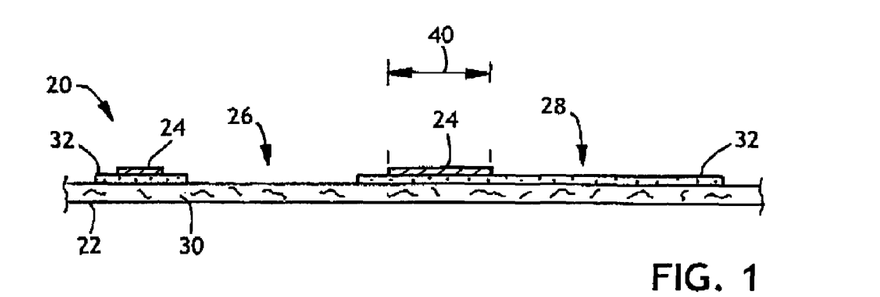
FIG. 1 shows an end view of a representative article in which a matrix-substrate includes a first matrix-region and at least a second matrix-region, where at least the second matrix-region has been treated to include at least a supplemental material to accommodate an electrically-conductive material.

FIG. 1 representatively shows a configuration in which the supplemental material 32 includes fibers or is otherwise configured to be fibrous. As illustrated in the shown example, the fibrous base material 30 can also include a nonwoven fabric. Suitable nonwoven base-fabrics may include spunbond fabrics, bonded-carded-web fabrics or the like, as well as combinations thereof.

The fibrous supplemental material 32 may include a nonwoven fibrous material that is provided separate from the base material. Suitable supplemental materials can, for example, include nonwoven fabrics, layers or strata of meltblown fibers or the like, as well as combinations thereof. In a desired feature, the layer of the fibrous supplemental material 32 can provide a more continuous or otherwise improved support for the electrically-conductive material that is applied to the supplemental material 32.

In a desired, representative arrangement, the matrix-substrate 22 can have a base material which includes a spunbond fabric, and the supplemental material can include a separately provided, fibrous meltblown layer. The layer of meltblown fibers can have a relatively low porosity and relatively low permeability with regard to the applied, electrically-conductive ink. The porosity and permeability of the meltblown material can, for example, be adjusted by controlling the pattern and density of the meltblown material. In a desired aspect, the meltblown material can be configured to operatively bridge across the surface-interstices of the material in the second matrix-region to support the electrically-conductive region in a configuration that has a desired resistivity.

The conductive ink or other conductive material can be applied to the layer of meltblown fibers during the manufacturing process at a location which is near and subsequent to the point at which the meltblown fibers are applied to the base material 30. For example, the conductive ink sprayed or otherwise printed at a location which is after and proximate to the point at which a layer of meltblown fibers is formed on a spunbond fibrous layer of base material 30.

Figure 2:
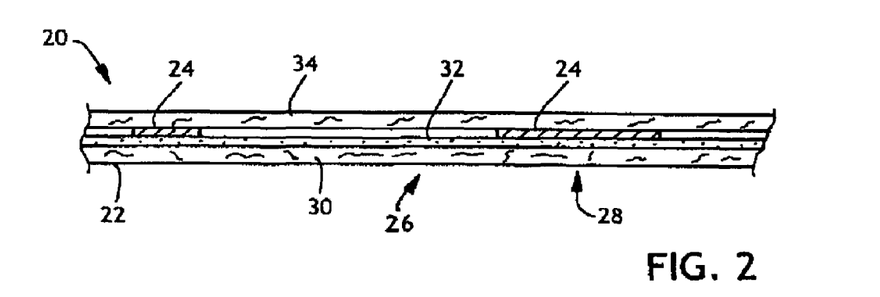
FIG. 2 shows a representative end side view in which a layer of auxiliary material can be applied or otherwise configured to operatively sandwich a layer of supplemental material between the auxiliary material and a layer of base material.

In another feature, a separately provided layer of auxiliary material 34 can be applied or otherwise configured to operatively sandwich the supplemental material 32 between the auxiliary material and the base material 30, as representatively shown in FIG. 2. Additionally, the electrically-conductive material may be sandwiched between the supplemental material 32 and the auxiliary material 34.

In optional arrangements, the article 30 can further comprise a third matrix-region. In particular configurations, the third matrix-region can include a third fibrous layer. Other aspects can have a first matrix-region which includes a first fibrous layer, and a second matrix-region which includes a second fibrous layer containing meltblown fibers. In a further aspect, the second matrix-region can be sandwiched between the first matrix-region and the third matrix-region.

In alternative arrangements, a sandwiched configuration of the supplemental material 32 between the base material 30 and auxiliary material 34 can be configured to provide an elastic material that can elastomerically stretch in one or more directions. Such stretchable materials can have the configuration of a neck-bonded laminate (NBL), a stretch-bonded-laminate (SBL) or a vertical filament laminate (VFL). Accordingly, the stretchable material can contain strips and other regions of electrically-conductive material.

Figure 3:
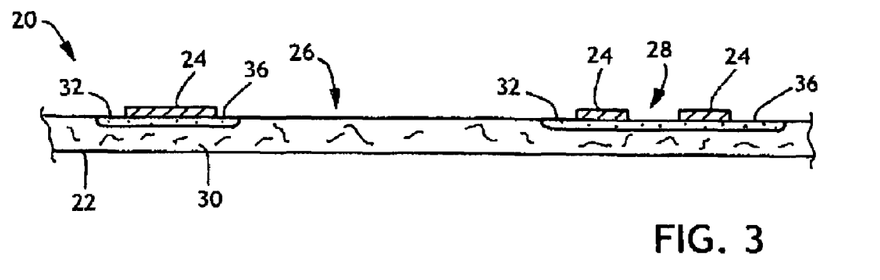
FIG. 3 shows a representative end view of an article in which at least the second matrix-region has a treatment with a supplemental material which substantially excludes fibers and operatively fills the void spaces of surface-interstices.

FIG. 3 representatively shows a configuration where at least the second matrix-region 26 has a treatment with a supplemental material 32 which substantially excludes fibers or is otherwise configured to be substantially nonfibrous. As representatively shown, the first matrix-region 26 can include a first fibrous or nonfibrous layer having a plurality of surface-interstices. Additionally, the second matrix-region 28 can include a corresponding fibrous or nonfibrous layer having a plurality of surface-interstices. The second matrix-region can further include a supplemental filler material that operatively fills the void spaces of the surface-interstices. Accordingly, the filler material can help bridge across at least the surface-interstices of the second matrix-region. In a particular aspect, the supplemental filler material can operatively bridge across the surface-interstices to support the electrically-conductive region in a configuration that has a desired resistivity.

The surface voids or other surface interstices in the porous substrate material can be filled by the supplemental material 32 in selected, local areas to create landing zones 36 that are operatively non-porous. Conductive ink or other electrically-conductive material can then be printed on or otherwise applied to landing zones 36. The majority of the base material of the matrix-substrate 22 can remain significantly more porous, and a relatively small percentage of the overall, total surface area of the matrix-substrate 22 may be operatively filled in by the selected supplemental filler material.

The landing-zone fill material can include any operative material, and can desirably be applied while the filler material is in a liquid or semi-solid form. Suitable filler materials can include a wax material, a hotmelt adhesive material, a synthetic polymer material or the like, as well as combinations thereof. The conductive ink or other electrically-conductive material that is applied to an individual landing zone 36 can be configured to penetrate the landing zone or to extend over or around a terminal edge of the landing zone to provide conductivity through the thickness dimension of the substrate material from one major facing surface to an opposite facing surface.

The filler material can have a selected melting point temperature. In particular aspects, the melting point temperature can be at least a minimum of about 38° C. The melting point temperature can alternatively be at least about 50° C., and can optionally be at least about 60° C. to provide desired benefits. In other aspects, the melting point temperature can be up to a maximum of about 150° C., or more. The melting point temperature can alternatively be up to about 140° C., and can optionally be up to about 130° C. to provide desired effectiveness.

The melting point can be selected to conveniently allow a deposition or other application of the filler material to the second matrix-region while the filler material is in a liquid or other operatively viscous state.

Figure 4:
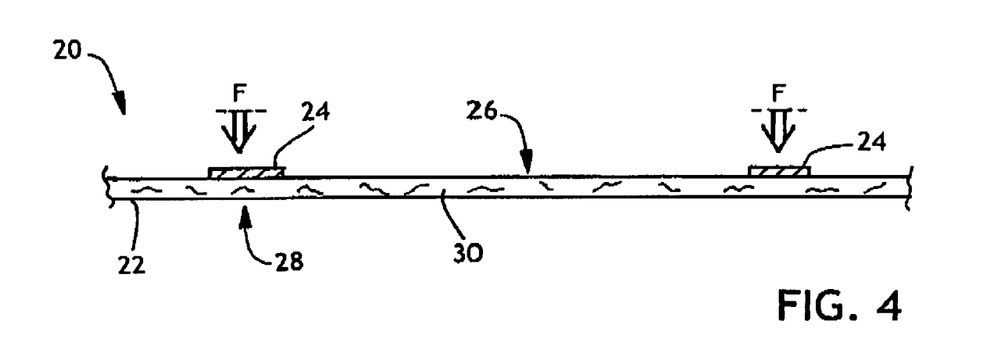
FIG. 4 shows a representative end view of an article having at least one matrix-region where an electrically-conductive material is initially applied to a surface of the selected matrix-region for a subsequent integration into a composite material by applying an operative force.
Figure 4A:
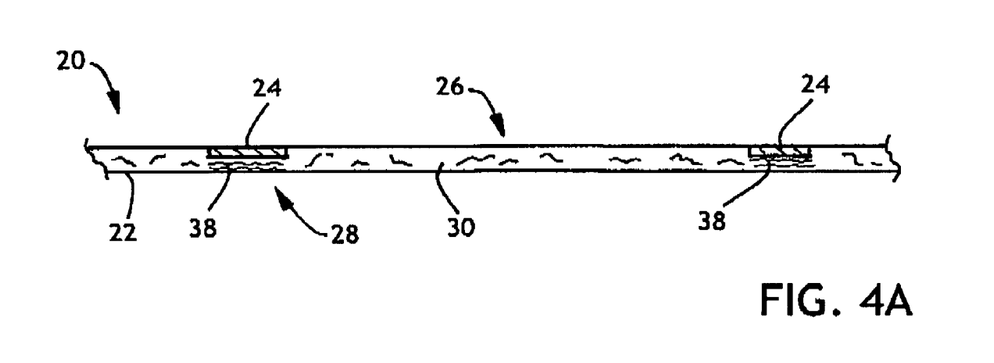
FIG. 4A shows a representative end view of an article having the electrically-conductive material integrated into a composite material.

With reference to FIGS. 4-4A, at least one selected matrix-region can include a treatment where a conductive ink or other electrically-conductive material is operatively consolidated with one or more of the substrate materials. For example, the electrically-conductive material can be operatively consolidated with the second matrix-region 28. The electrically-conductive material in an individual, electrically-conductive region 24 can be initially applied to a surface of the selected matrix-region and the materials in the selected matrix-region (e.g. in the second matrix-region 28) can be fused, or otherwise integrated or combined into a composite material 38 by applying an operative, compressive force F.

The base substrate materials in the selected matrix-region can include any suitable material. Such materials can, for example, include an SMS material, a polymer film material, a non-woven fabric material or the like, as well as combinations thereof. The material may also be elastomeric, and may include one or more layers or strata. Such material can, for example, include a NBL material, a SBL material a VFL material or the like, as well as combinations thereof. For example, the selected matrix-region can include a spunbond fabric, base material, and a fibrous meltblown layer. The electrically-conductive material can be applied to the meltblown layer.

The force F can be generated by any operative technique. Such techniques can, for example, include ultrasonic techniques, mechanical pressure techniques, fluid pressure techniques or the like, as well as combinations thereof. The forcing of the conductive material into the material of the selected matrix-region can, for example, increase the density of the electrically-conductive material so that the conductive material will more effectively maintain a desired high conductivity and low resistivity value (e.g. ohms per unit length of conductor) while the electrically-conductive region is positioned operatively adjacent the second matrix-region and configured for its intended use. It can also provide an improved ability to access the conductive path in the substrate material from one or both faces, depending on the application. The forcing of the electrically-conductive material into the composite material 38 can be controlled by adjusting selected parameters. Such parameters can, for example, include the add-on amount of a conductive ink, the fusion or forcing pressure applied to form the composite material 38, the geometry of the forcing device and the ink particle size compared to the size of the interstices in the matrix substrate material, as well as other parameters.

Accordingly, the article 20 can have a first matrix-region, and at least a second matrix-region. The first matrix-region can include a first fibrous layer, and the second matrix-region can include a second fibrous layer. The electrically-conductive material has been applied to the matrix material in the selected matrix-region. Additionally, the second matrix-region and the applied, electrically-conductive material have been operatively compacted together to provide the resistivity of the electrically-conductive region.

In another aspect, the second matrix region 28 can be modified by melting, glassifying or fusing fibers to create an operative landing zone that is operatively non-porous (e.g. a landing zone having a fused area 38). Conductive ink or other electrically-conductive material can then be subsequently printed on or otherwise applied to landing zones. The majority of the base material of the matrix-substrate 22 can remain significantly more porous, and a relatively small percentage of the overall, total surface area of the matrix-substrate 22 may be operatively filled in with the fused material. In particular arrangements, supplemental material may be added to help provide the desired low porosity in the fused areas.

The second matrix-region can include a second fibrous layer having a selected basis weight. In particular aspects, the basis weight of the second fibrous layer can be at least a minimum of about 5 $g/m^2$. The basis weight can alternatively be at least about 10 $g/m^2$, and can optionally be at least about 15 $g/m^2$ to provide desired benefits. In other aspects, the basis weight of the second fibrous layer can be up to a maximum of about 130 $g/m^2$, or more. The basis weight can alternatively be up to about 45 $g/m^2$ or 60 $g/m^2$, and can optionally be up to about 30 $g/m^2$ to provide desired effectiveness. In another feature, second matrix-region can be operatively compacted to provide a selected composite density.

A further feature can include a matrix-substrate 22 having a selected resistivity value. Accordingly, at least the substrate portion of the first matrix-region 26, second matrix-region 28 and/or other matrix-region can have the selected resistivity value. In a particular aspect, the resistivity value can be at least a minimum of about 5 mega-ohms per meter ($M\Omega/m$). The resistivity value can alternatively be up to about 10 $M\Omega/m$, and can optionally be up to about 100 $M\Omega/m$, or more, to provide desired performance. In desired arrangements, the resistivity value of matrix-substrate 22, particularly in the first matrix-region 26, can be at least about one order of magnitude (10 times) greater than a resistivity value of the electrically conductive region 24. The resistivity value of matrix-substrate 22 can alternatively be at least about 100 times greater than the resistivity value of the electrically conductive region 24, and can optionally be at least about 1000 times greater than the resistivity value of the electrically conductive region to provide improved benefits.

An individual, electrically-conductive region 24 can have a selected electrical resistance per unit length value. In a desired aspect, the resistance per unit length value can be substantially zero $\Omega/m$ (ohms/meter). In other aspects, the electrical resistance per unit length value can be not more than a maximum of about 1 $M\Omega/m$ (mega-ohms/meter). The resistance per unit length value can alternatively be not more than about 1 $K\Omega/m$ (kilo-ohms/meter), and can optionally be not more than about 100 $\Omega/m$ to provide improved effectiveness.

In another aspect, the resistivity value of an individual, electrically-conductive region 24 can be substantially zero ohms per square per mil of the electrically-conductive material ($\Omega$/square per mil), where: 1 mil=0.001 inch. The resistivity value can alternatively be as low as 0.1 $\Omega$/square per mil, and can optionally be as low as 1 $\Omega$/square per mil. In still other aspects, the resistivity value can be not more than a maximum of about 33 K$\Omega$/square per mil. The resistivity value can alternatively be not more than about 16 K$\Omega$/square per mil, and can optionally be not more than about 8 K$\Omega$/square per mil to provide improved effectiveness.

A suitable procedure for determining the resistivity values in terms of "ohms per square per mil" is *ASTM F* 1896-98 (Reapproved 2004), *Test Method for Determining the Electrical Resistivity of a Printed Conductive Material.*

In a desired feature, the electrically-conductive region can have a relatively longer length-dimension and a relatively shorter cross-deckle, width dimension 40. The electrically-conductive region can extend lengthwise along a substantially continuous electrically-conductive path length-dimension of at least about 0.1 cm. The electrically-conductive path-length can alternatively be at least about 1 cm, and can optionally be at least about 100 cm. In another feature, the electrically-conductive path-length can alternatively be up to about 1000 cm or more.

A further feature can include an electrically-conductive region 24 having a cross-deckle dimension 40 of up to about 10 cm. The cross-deckle dimension can alternatively be about 5 cm or less, and can optionally be about 1 cm or less to provide desired benefits. Additionally, the cross-deckle dimension can be as low as 0.1 cm or less.

It should be readily appreciated that the length, width and other dimensions of an individual, electrically-conductive region can be determined by employing standard microscopy techniques. Such techniques are conventional, and are well known in the art.

Figure 5:
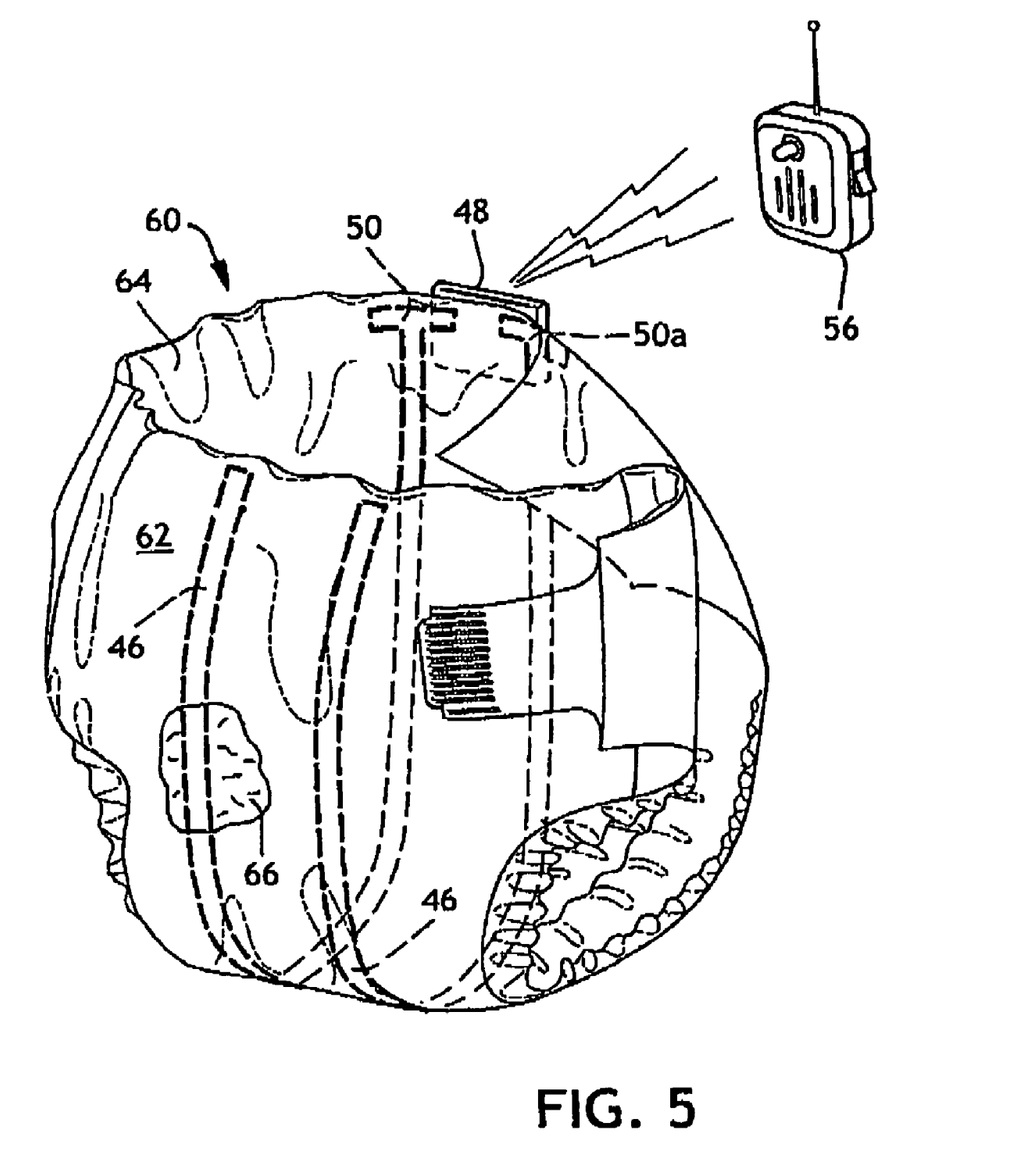
FIG. 5 shows a partially cut-away, perspective view of a representative article having a sensor or other external electrical monitoring device that is positioned on an inward side surface of the insulating substrate and interconnects along a conductive pathway through the substrate to a circuit-path and cooperating processor that is positioned on an opposite, outward side of the substrate.
Figure 6:
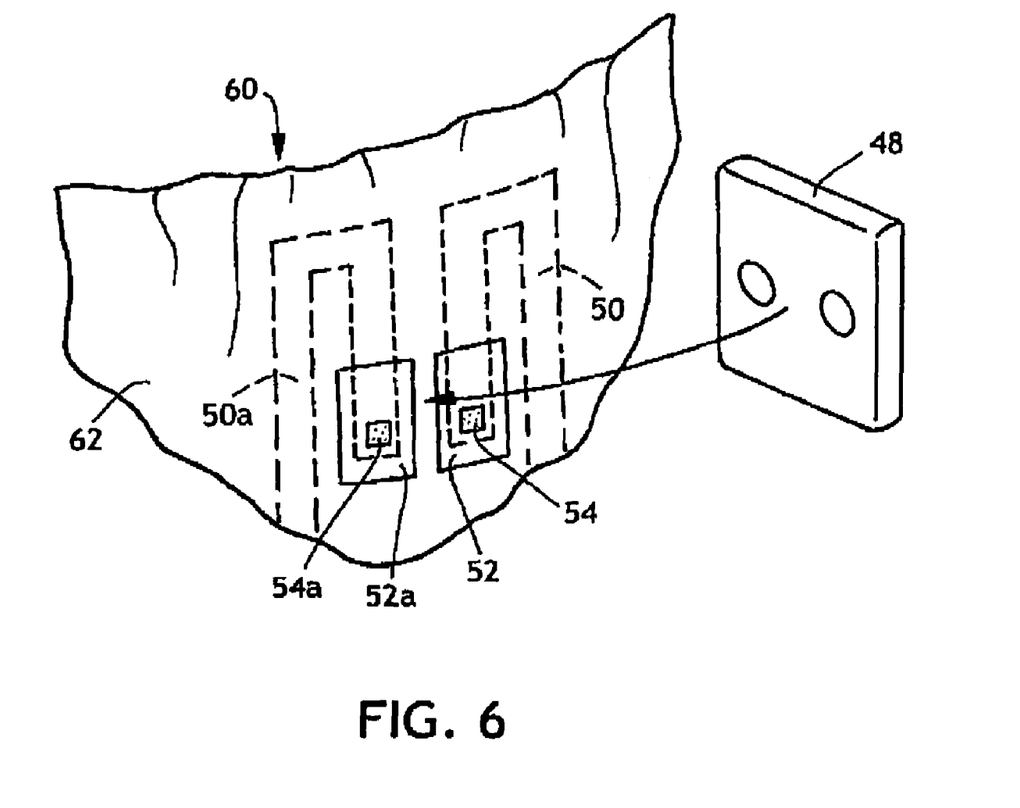
FIG. 6 shows a perspective, partial view of another representative arrangement of a first-circuit path that is positioned on a conductive bond-path through the substrate to a second circuit-path and cooperating processor that is positioned on an opposite, outward-side surface of the substrate.

With reference to FIGS. 5 and 6, another aspect of the article can include at least one electrically-conductive circuit-path 50 or other electrically-conductive region which has been operatively connected to a sensor mechanism 46 which can provide selected sensor data. In a further aspect, at least another electrically-conductive circuit-path 52 can be operatively connected to an electronic processor mechanism 48 which can operatively receive the sensor data and provide selected signal data.

Any appropriate detecting, sensing or interrogating device or system may be operatively employed to provide the sensor mechanism 46 that is incorporated with the method. A suitable sensor mechanism can, for example, include a wetness sensor, a motion sensor, a temperature sensor, a humidity sensor, a pressure sensor, a position sensor, a proximity sensor, a light sensor, an odor sensor or the like, as well as combinations thereof.

It should be appreciated that any appropriate information or data may be operatively included in the sensor data that is generated with the method. Suitable sensor data can, for example, include data regarding resistance, voltage, capacitance, inductance, wetness, motion, temperature, humidity, pressure, position, proximity, light, odor or the like, as well as combinations thereof.

Any appropriate analyzing, computing or assessing device or system may be operatively included with the electronic processor mechanism 48. A suitable electronic processor mechanism can, for example, include a micro controller, a micro processor, an analog to digital converter, a FPGA (Field Programmable Gate Array), an EEPROM (Electrically Erasable Programmable Read-Only Memory), an electronic memory device or the like, as well as combinations thereof. The electronic processor can collect, process, store, analyze, convert digital or analog data, provide feedback or the like, as well as combinations thereof.

It should be appreciated that any appropriate information or data may be operatively included in the signal data that is generated with the method. Suitable signal data can, for example, include data pertaining to light, sound, tactile, odor, electrical impulses, biometric data, motion, vibration, wireless communication or the like, as well as combinations thereof.

In desired arrangements, the electronic processor mechanism 48 may be configured to transfer the signal data to another, relatively remote location. As representatively shown, for example, the method of the invention may be configured to transmit signal data with a wireless communication link to a remote receiver device 56.

A suitable product article, such as the representatively shown personal care article, can be configured to incorporate the present invention. As illustrated, the product article 60 may, for example, be configured to provide an infant diaper or a child-care training pant. The product article can have an outercover layer 62, and a first circuit-path 50 disposed along a selected bodyside or outward-side surface of a nonwoven fabric component. Optionally, the product article can include one or more second circuit-paths 52 disposed along an outward, garment-side surface of the outercover. As representatively shown, the product article may include one or more supplemental, first circuit-paths 50a which are disposed along a selected surface of a selected nonwoven fabric component, and one or more supplemental, second circuit-paths 52a disposed along an outward, garment-side surface of the outercover.

In a particular configuration, the first circuit-paths 50 and 50a can be operatively connected to a selected sensor mechanism. In the representatively shown arrangement, for example, the sensor mechanism can be a wetness sensor. The sensor mechanism can, for example, be configured to provide one or more of functions or operations pertaining to a wireless, audio, visual and/or tactile indication of a monitored event. Additionally, the sensor mechanism can, for example, be configured to provide one or more of functions or operations pertaining to a number of events, lengths of time between events, as well as any other statistics pertaining to a selected event, as desired by a user. As representatively shown, for example, the sensor mechanism can be an internal sensor that is configured to detect a presence of aqueous liquid, which is within the product article 60 and is present above a selected threshold level.

Additionally, the circuit-paths 50 and 50a can be operatively connected to the selected electronic processor mechanism 48. In the representatively shown arrangement, for example, the electronic processor mechanism can be a microcontroller, and suitable circuitry can extend through the thickness of intervening components to interconnect the first circuit-paths 50 to the second circuit-paths 52. Additionally, the electronic processor mechanism can be selectively connected to the cooperating circuit-paths to provide desired operability. The electronic processor mechanism can, for example, be configured to convert data (Analog to Digital, or Digital to Analog), store data, trigger a predetermined response, allow for user interrupt, provide signal conditioning, compute and process algorithms or the like, as well as combinations thereof.

As representatively shown, at least a selection portion of the first circuit-path (50 and/or 50a) is positioned proximally adjacent at least an operative portion of the second circuit-path (52 and/or 52a) at a first predetermined electrical bond location. The outercover 62 has a position that is interposed between the first and second circuit-paths, and is composed of a material that provides an electrically-insulating barrier layer which is interposed between the first circuit-path and second circuit-path at the first bond location. The first circuit-paths 50 and/or 50a are configured to operatively connect to the second circuit-paths 52 and/or 52a through the thickness dimension of the outercover 62 with a mechanical bond positioned at the first bond location. Desirably, the mechanical bond includes an ultrasonic bond. The mechanical bonding is configured to provide an electrically conductive bond-path 54 between the appointed first circuit-path and the appointed second circuit-path at the first bond location.

An example of a suitable technique for providing an electrically-conductive bond-path through an intervening layer of insulating material is described in U.S. patent application Ser. No. 11/514,541 entitled ELECTRICAL CONDUCTIVITY BRIDGE IN A CONDUCTIVE MULTILAYER ARTICLE by Darold Tippey, et al., which was filed Aug. 31, 2006. The entire disclosure of this document is incorporated herein by reference in a manner that is consistent herewith.

As representatively, shown, a separately provided, external, electronic processor mechanism 48 can be operatively connected to the second circuit-paths 52 and/or 52a. In desired arrangements, the electronic processor mechanism 48 can be removably attached or otherwise removably connected to the second circuit-paths 52 and/or 52a on the outside surface of the outercover 62. Accordingly, the electrically conductive bond-path can be employed to operatively connect the internally positioned sensor mechanism to the separately provided, external, electronic processor mechanism with an operative, electrically-conductive connection.

The product article 60 can also include a topsheet or bodyside liner layer 64, and an absorbent structure 66 positioned between the outercover layer 62 and topsheet layer 64. Additionally, the product article 60 can include other components, such as fasteners, elastic members, transfer layers, distribution layers or the like, as desired, in a conventional arrangement that are well known in the art.

The outercover layer 62 may be constructed of any operative material, and may or may not be configured to be operatively liquid-permeable. In a particular configuration, the outercover layer 62 may be configured to provide an operatively liquid-impermeable layer. The outercover layer may, for example, include a polymeric film, a woven fabric, a nonwoven fabric or the like, as well as combinations or composites thereof. For example, the outercover layer 62 may include a polymer film laminated to a woven or nonwoven fabric. In a particular feature, the polymer film can be composed of polyethylene, polypropylene, polyester or the like, as well as combinations thereof. Additionally, the polymer film may be micro-embossed. Desirably, the outercover layer 62 can operatively permit a sufficient passage of air and moisture vapor out of the product article, particularly out of an absorbent (e.g. storage or absorbent structure 66) while blocking the passage of bodily liquids.

The topsheet layer 64 may be constructed of any operative material, and may be a composite material. For example, the topsheet layer can include a woven fabric, a nonwoven fabric, a polymer film, or the like, as well as combinations thereof. Examples of a nonwoven fabric include, spunbond fabric, meltblown fabric, coform fabric, a carded web, a bonded-carded-web, or the like as well as combinations thereof. For example, the topsheet layer can include a woven fabric, a nonwoven fabric, a polymeric film that has been configured to be operatively liquid-permeable, or the like, as well as combinations thereof. Other examples of suitable materials for constructing the topsheet layer can include rayon, bonded carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof.

The topsheet layer 64 can also have at least a portion of its bodyside surface treated with a surfactant to render the topsheet more hydrophilic. The surfactant can permit arriving bodily liquids to more readily penetrate the topsheet layer. The surfactant may also diminish the likelihood that the arriving bodily fluids, such as menstrual fluid, will flow off the topsheet layer rather than penetrate through the topsheet layer into other components of the product article (e.g. into the absorbent body structure 66). In a particular configuration, the surfactant can be substantially evenly distributed across at least a portion of the upper, bodyside surface of the topsheet layer 64 that overlays the upper, bodyside surface of the absorbent.

The topsheet layer 64 typically extends over the upper, bodyside surface of the absorbent structure, but can alternatively, further extend around the product article to partially or entirely, surround or enclose the absorbent structure. Alternatively, the topsheet layer 64 and the outercover layer 62 can have peripheral margins which extend outwardly beyond the terminal, peripheral edges of the absorbent structure 66, and the extending margins can be joined together to partially or entirely, surround or enclose the absorbent structure.

The structure of the absorbent body 66 can include a matrix of absorbent fibers and/or absorbent particulate material. The absorbent fiber can include natural or synthetic fiber. The absorbent structure 66 may also include superabsorbent material, and the superabsorbent material may be in the form of particles having selected sizes and shapes. Superabsorbent materials suitable for use in the present invention are known to those skilled in the art. As a general rule, the water-swellable, generally water-insoluble, hydrogel-forming polymeric absorbent material (superabsorbent) is capable of absorbing at least about 10, desirably about 20, and possibly about 100 times or more its weight in water. Additionally, the absorbent body structure 66 can comprise a composite. The absorbent composite can, for example, include an intake layer, a distribution layer and/or a storage/retention layer, as desired.

An example of a personal care article that includes a sensor system is described in U.S. patent application Ser. No. 11/303,283 entitled GARMENTS WITH EASY-TO-USE SIGNALING DEVICE by Andrew Long, et al. which was filed Dec. 15, 2005. The entire disclosure of this document is incorporated herein by reference in a manner that is consistent herewith.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

The invention claimed is:

1. A limited use, disposable article, comprising
a matrix-substrate which includes a substantially continuously extending network of matrix-material;
an electrically-conductive region of a separately provided, electrically-conductive material that has been operatively applied to the matrix substrate from a viscous configuration of the electrically-conductive material;
wherein
the matrix-substrate includes a first matrix-region, and at least a second matrix-region;
at least the second matrix-region includes a treatment that provides for an operative formation of a selected resistivity in the electrically-conductive region;
the first matrix-region has a resistivity value of at least about 5 MΩ/m;
the electrically-conductive region is positioned operatively adjacent the second matrix-region;
the electrically-conductive region has an operatively low resistivity value, as determined when the electrically-conductive region is positioned operatively adjacent the second matrix-region and configured for its intended use.

2. An article as recited in claim 1, wherein the electrically-conductive region has resistivity value of not more than about 1 MΩ/m.

3. An article as recited in claim 1, wherein the electrically-conductive region has resistivity value of not more than about 33 KΩ/square per mil.

4. An article as recited in claim 1, wherein the electrically-conductive region has a corresponding resistivity value, and the first matrix-region has a resistivity value which is at least about 10 times the resistivity value of the electrically-conductive region.

5. An article as recited in claim 1, wherein the second matrix region has a basis weight of up to about 130 g/m².

6. An article as recited in claim 1, wherein the matrix-material has been configured to provide interconnected plurality of matrix elements.

7. An article as recited in claim 1, wherein the matrix-material has been configured to provide interconnected plurality of fibers.

8. An article as recited in claim 1, wherein
the first matrix-region includes a first fibrous region;
the second matrix-region includes a second fibrous region.

9. An article as recited in claim 8, wherein the second matrix-region includes a layer of meltblown fibers.

10. An article as recited in claim 1, further comprising a third matrix-region, wherein
the first matrix-region includes a first fibrous region;
the second matrix-region includes a second fibrous layer containing meltblown fibers;
the third matrix-region includes a third fibrous region;
the second matrix-region is sandwiched between the first matrix-region and the third matrix-region.

11. An article as recited in claim 1, wherein
the first matrix-region includes a first fibrous region having a plurality of surface-interstices;
the second matrix-region includes a filler material that operatively bridges across the surface-interstices of the second matrix-region to support the electrically-conductive region in a configuration that has a resistivity value of not more than about 1 MΩ/m.

12. An article as recited in claim 11, wherein the filler material has a melting point temperature of at least about 38° C.; and has been applied to the second matrix-region from a liquid state.

13. An article as recited in claim 12, wherein the filler material includes a wax or hotmelt adhesive.

14. An article as recited in claim 1, wherein
the first matrix-region includes a first fibrous region having a basis weight of up to about 130 g/m²;
the second matrix-region includes a second fibrous region having a basis weight of up to about 130 g/m².

15. An article as recited in claim 1, wherein
the first matrix-region includes a first fibrous region;
the second matrix-region includes a second fibrous region;
the second matrix-region and the applied, electrically-conductive material have been operatively compacted together to provide the resistivity of the electrically-conductive region.

16. An article as recited in claim 1, wherein the electrically-conductive material has been applied to the matrix substrate from an operatively liquid configuration of the electrically-conductive material.

17. An article as recited in claim 1, wherein the electrically-conductive material includes an electrically-conductive ink material that has been printed onto the matrix substrate.

18. A limited use, disposable article, comprising
a matrix-substrate provided by a substantially continuously extending network of interconnected matrix elements that include matrix-material;
an electrically-conductive region of a separately provided, electrically-conductive material that has been applied to the matrix substrate from an operatively liquid configuration of the electrically-conductive material;
wherein
the matrix-substrate includes a first matrix-region and at least a second matrix-region;
at least the second matrix-region includes a treatment that provides for an operative formation of a selected resistivity in the electrically-conductive region;
the first matrix-region has a resistivity value of at least a minimum of about 5 MΩ/m;
the second matrix-region has a resistivity value of at least a minimum of about 5 MΩ/m;
the electrically-conductive region is positioned operatively adjacent the second matrix-region;
the electrically-conductive region has a resistivity value of not more than about 1 Ω/m, as determined when the electrically-conductive region is positioned operatively adjacent the second matrix-region and configured for its intended use; and
the resistivity value of the first matrix-region is at least about 10 times the resistivity value of the electrically-conductive region.

19. An article as recited in claim 18, wherein
the first matrix-region includes a first fibrous region;
the second matrix-region includes a second fibrous region containing meltblown fibers.

20. An article as recited in claim 18, wherein
the first matrix-region includes a first fibrous region having a plurality of surface-interstices;
the second matrix-region includes a filler material that operatively bridges across the surface-interstices of the second matrix-region to support the electrically-conductive region in a configuration that has a resistivity value of not more than about 1 KΩ/m.

* * * * *